United States Patent [19]

Sundsmo et al.

[11] Patent Number: 4,760,131

[45] Date of Patent: Jul. 26, 1988

[54] WOUND-HEALING COMPOSITION

[75] Inventors: John S. Sundsmo, Pleasanton; George A. Ksander, Menlo Park; John M. McPherson, Sunnyvale, all of Calif.

[73] Assignee: Collagen Corporation, Palo Alto, Calif.

[21] Appl. No.: 877,266

[22] Filed: Jun. 23, 1986

Related U.S. Application Data

[63] Continuation-in-part of Ser. No. 855,508, Apr. 23, 1986, abandoned.

[51] Int. Cl.$^4$ .................. C07G 7/00; A61K 37/12
[52] U.S. Cl. ............................ 530/356; 514/2; 514/21; 514/54; 514/56; 514/62; 514/801; 128/DIG. 8; 128/156; 427/2
[58] Field of Search ............... 530/356, 840; 514/2, 514/21, 54, 56, 62, 801; 128/DIG. 8, 156; 427/2

[56] References Cited

U.S. PATENT DOCUMENTS

| | | | |
|---|---|---|---|
| 3,694,161 | 9/1972 | Kleszynski et al. | 436/70 |
| 4,060,081 | 11/1977 | Yannas et al. | 128/156 |
| 4,350,629 | 9/1982 | Yannas et al. | 530/356 |
| 4,418,691 | 6/1983 | Yannas et al. | 128/156 |
| 4,448,718 | 5/1984 | Yannas et al. | 530/356 |
| 4,453,939 | 6/1984 | Zimmerman et al. | 604/368 |
| 4,458,678 | 7/1984 | Yannas et al. | 128/155 |
| 4,505,266 | 3/1985 | Yannas et al. | 128/1 R |

FOREIGN PATENT DOCUMENTS 85301127 9/1985 European Pat. Off. .

OTHER PUBLICATIONS

Shoshan, Shmuel, International Review of Connective Tissue Research, vol. 9, pp. 1–26 (1981).
Hunt, T. K. et al., eds., Soft and Hard Tissue Repair, Praeger Publishers, (1984), pp. 381–394.

*Primary Examiner*—Delbert R. Phillips
*Assistant Examiner*—Nathan M. Nutter
*Attorney, Agent, or Firm*—Ciotti & Murashige, Irell & Manella

[57] ABSTRACT

A soft tissue wound healing composition comprising an aqueous mixture of fibrillar collagen, heparin, and undegranulated platelets or platelet releasate. The composition is applied topically to the wound site in conjunction with means to keep it at the site and hydrated or in the form of an occlusive dressing.

24 Claims, 4 Drawing Sheets

WOUND-HEALING COMPOSITION

CROSS-REFERENCE TO RELATED APPLICATION

This application is a continuation-in-part of copending application Ser. No. 855,508, filed Apr. 23, 1986 and now abandoned.

DESCRIPTION

1. Technical Field

The invention is in the fields of medicine, surgery, and biochemistry. More particularly, it concerns wound healing compositions comprising fibrillar collagen, heparin, and platelets or platelet releasate.

2. Background

The process of wound healing consists of a chronological sequence of events characterized by the various cellular infiltrates that appear within the wound. Immediately after wounding, the process of coagulation involves both the humoral aspects of coagulation and the cellular response. The principal cellular response concerns the interaction of platelets with coagulation proteins, thrombin and collagen. Once the coagulation process is completed, various types of leukocytes appear in the wound in an orderly and reproducible sequence. Fibroblasts, endothelial cells, and capillaries appear in the wound slightly later than leukocytes. The fibroblasts are responsible for the formation of the connective tissue components, specifically, collagen and the glycosaminoglycans, and, at a much later stage, for the formation of elastic fibers.

Wound healing is thus a complex process at the cellular level involving primarily fibroblasts and epithelial cells with additional effects being exerted by platelets, macrophages, neutrophils, endothelial cells, myofibroblasts, and perhaps other unidentified cell types. At a biochemical level the processes involved in wound healing are poorly understood, although it is clear that growth factors such as transforming growth factor (TGF), platelet-derived growth factor (PDCF), and epidermal growth factor exert effects on these cells in vitro. It is known that the platelets contain growth factors but it has not been determined whether these factors are normally released at wound sites. Collagen is known to induce platelet aggregation and degranulation reactions in vitro, but again it is not clear whether these reactions also occur in vivo at local wound sites. In sum, a comprehensive biochemical analysis of wound healing has not been accomplished, although it is presumed that the in vitro biological activities of platelets are operative in vivo.

Several prior patent publications have suggested using combinations of collagen and glycosaminoglycans to promote wound healing. Yannas et al have issued a series of U.S. patents describing laminated composites that may be used as synthetic skin. The first of the series, U.S. Pat. No. 4,060,081 describes a composite in which the bottom (skin side) layer is collagen cross-linked with a glycosaminoglycan. The glycosaminoglycan is added to solubilized collagen to form a precipitate, the precipitate is homogenized and then cross-linked with glutaraldehyde. U.S. Pat. No. 4,350,629 describes a variation of this process in which the glutaraldehyde is added before the glycosaminoglycan is added to the collagen. U.S. Pat No. 4,418,691 describes yet another variation in which the collagen-glycosaminoglycan lattice is impregnated with viable epithelial, mesenchymal, or fibroblast cells.

European Patent Application No. 85301127 (published Sept. 11, 1985 under No. 154447) describes a wound healing composition that consists of a suspension of collagen and a glycosaminoglycan such as heparin or heparan sulfate that induces chemotaxis. Of the previously described wound healing compositions, this composition is the most closely related to the present invention. As shown hereinafter, however, in vivo testing of collagen-glycosaminoglycan suspensions failed to cause any major change in the rate or extent of wound healing in experimental animals.

Soft and Hard Tissue Repair (Hunt, T. K. et al, eds) Praeger Publishers, New York (1984), pp. 381–394 describes the role of platelets and platelet constituents in wound repair.

The present invention provides a wound healing composition whose biological activity is vastly superior to the suspensions described in the mentioned European Patent Application. This new composition promotes re-epithelialization, fibroplasia, granulation tissue deposition, vascularization and new host collagen synthesis at wound sites. The granulation tissue is highly organized, even at early time points after initiation of treatment, which contributes to an overall appearance of increased wound strength at early times, and the appearance of a greater extent of wound healing at any given time. The composition also decreases the total time required for wound healing and wound repair, apparently by promoting the rate of wound healing. The composition is self-limiting, being active only at wound sites, eliminating the adverse possibility of disseminated subcutaneous growth effects.

DISCLOSURE OF THE INVENTION

The present invention is a soft tissue wound healing composition comprising an aqueous mixture of:

(a) fibrillar collagen at a concentration in the range of about 1 to about 70 mg/ml;

(b) about 0.1% to about 10% by weight based on collagen of heparin, a heparin-like glycosaminoglycan, or mixtures thereof; and (c) about 0.01% to about 10% by volume based on collagen of undegranulated platelets or an equivalent amount of platelet releasate.

Wound dressings comprising the above composition carried on a solid carrier and methods of promoting wound healing by applying the above composition or dressing topically to wounds are other aspects of the invention.

MODES OF CARRYING OUT THE INVENTION

Figure 1:
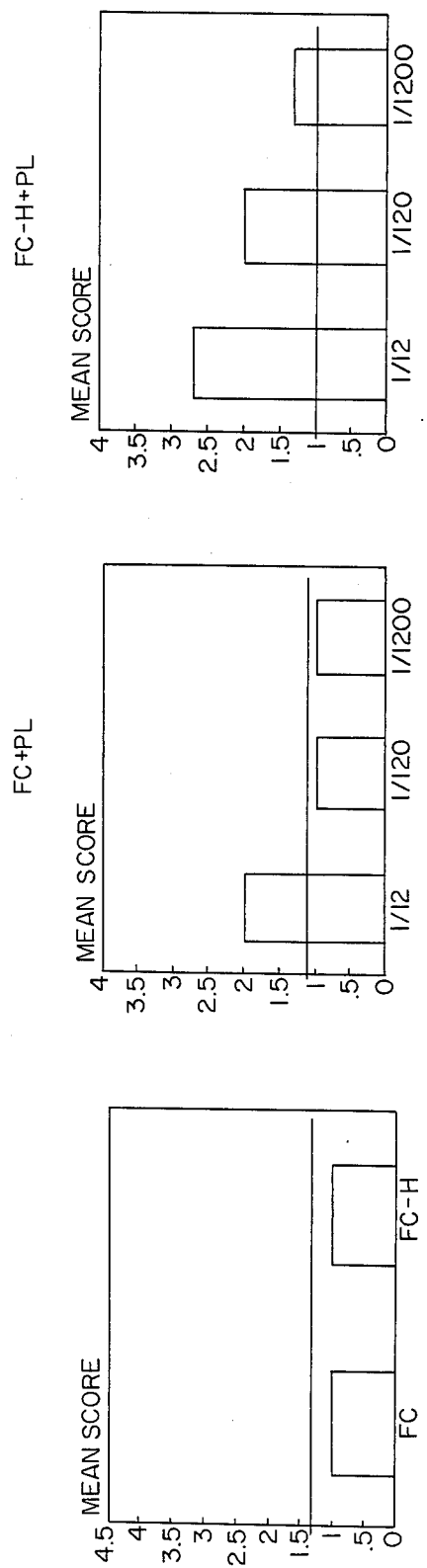
FIG. 1 is a set of bar graphs of results of the histological examinations reported infra showing the fibroplasia evident in histological sections of wound sites treated with various test compositions.

The composition of the invention is useful for treating soft tissue wounds such as cutaneous, dermal, mucosal or epithelial wounds in vertebrates. It is especially useful for treating cutaneous wounds in mammals including man, domestic and farm animals, sports animals, and pets. It may be used to treat any type of full or partial thickness cutaneous wounds including traumatic wounds, surgical wounds, thermal or chemical wounds (burns), radiation wounds and chronic ulcers such as decubiti, and cutaneous ulcers caused by vascular, hematologic and metabolic diseases, infections, or neoplasms.

The collagen that is used in the invention is fibrillar and is capable of binding heparin or heparin-like glycosaminoglycans. Type I or Type III collagen, or mixtures thereof, are preferred because of their heparin binding capacity. The collagen may be of genetically dissimilar origin (e.g., allogeneic or xenogeneic) than the individual to which it is applied. If the collagen is xenogeneic it is preferred that it be purified to lessen or reduce the likelihood of immunogenicity. The collagen fibers may be native or reconstituted and may be cross-linked or uncross-linked. Bovine dermal fibrillar collagen suitable for use in the composition is available commercially under the trademark ZYDERM® from the assignee of this application. The fibrillar collagen is in the form of an aqueous suspension or gel in which the concentration of collagen is in the range of about 1 to 70 mg/ml. A collagen concentration range of 15 to 35 mg/ml is preferred for handling purposes. Depending upon the concentration of collagen the consistency of the final mixture will range from a translucent gel to a runny syrup.

Heparin or a heparin-like glycosaminoglycan is mixed with the fibrillar collagen in amounts ranging between about 0.1% to about 10% by weight, based on collagen, preferably about 0.3% to 3%, and most preferably about 1%. Heparin is a staple product of commerce. Fragments and derivatives of heparin are known which possess chemical similarity to heparin. As used herein the term "heparin-like glycosaminoglycan" is intended to include such fragments and derivatives, provided they are functionally equivalent to heparin in the composition (i.e., combine with collagen and platelets to provide efficacious wound healing).

The platelets that are used in the invention are isolated from vertebrate blood, preferably mammalian blood, under conditions which prevent degranulation. Such conditions are well known and typically involve mixing the blood with an anticoagulant solution and centrifuging the platelets from the mixture. The mammalian species of the platelets are diluted in buffer and then added to the fibrillar collagen-heparin mixture. The final volume dilution of platelets, expressed in terms of volume of packed platelets, is in the range of about 1:10 to 1:10,000, preferably 1:50 to 1:100. Expressed in terms of volume % based on collagen, the packed platelets are added to the mixture at levels in the range of 0.01% to 10%, preferably 2% to 10%.

Platelet releasate may be used as an alternative to whole platelets. The releasate comprises granule constituents that are released after aggregation and that possess angiogenic activity, chemotactic activity, mitogenic activity, connective tissue deposition activity, or epidermal cell proliferation activity. It may be prepared by sonicating platelets or treating a platelet suspension with agents that cause the platelets to aggregate and release granule constituents. Examples of such agents are thrombin, collagen, ADP and immune complexes. After such treatment solids (e.g., cellular debris, aggregated platelets) are separated, such as by centrifugation. The releasate may be purified by affinity chromatography using a heparin-Sepharose column. The amount of releasate used in the mixture is that which is equivalent to 0.01% to 10% by volume, preferably 2% to 10%, based on collagen of packed platelets. In other words, one uses that amount of releasate that is derived from such an amount of packed platelets.

In addition to the fibrillar collagen, heparin, and platelets/platelet releasate, the composition will typically contain buffers and salts that maintain the aqueous mixture at approximately physiological pH and ionic strength (i.e., pH 6.8 to 7.4; ionic strength (r/2) 0.1 to 0.2). Minor amounts of other additives such as local anesthetics (e.g., lidocaine) bacteriostats, antibiotics, serum or plasma proteins, culture supernatants, cell extracts, gelling agents, and purified monocytes may be included in the wound healing composition.

A preferred storage temperature for the individual components of the composition and the final composition is 2° C. to 6° C.

The mixture of fibrillar collagen, heparin, and platelets/platelet releasate is applied topically to the wound site. The composition may be applied per se or in the form of an occlusive dressing. When applied per se the composition is applied as an ointment, gel, lotion or spray, depending upon its consistency. If the wound is depressed, the composition is packed into the wound. The composition is applied in conjunction with means for keeping the composition at the wound site and, in the case of open wounds, for maintaining the composition hydrated. For cutaneous wounds such means are exemplified by dressings, such as Opsite wound dressing, having a suitable water vapor transmission rate, or perhaps skin grafts or flaps that are placed over the composition.

When applied in the form of an occlusive dressing the composition is impregnated, coated, adsorbed or otherwise applied to a synthetic or natural solid support, such as a fibrous or nonfibrous backing or sponge, and the composite is applied to the wound site.

The following experiments further illustrate the invention and its relationship to the prior art. These experiments are not intended to limit the invention in any manner.

A. PREPARATION OF COLLAGEN-HEPARIN-PLATELET COMPOSITES

Test wound healing compositions were prepared in a stepwise manner. First, fibrillar collagen/heparin (FC-H) was prepared by mixing 10 ml of commercially available bovine dermal fibrillar collagen (FC; 35 mg/ml) with 1 ml of 3.3 mg/ml heparin (H)(Sigma, St. Louis, Mo.). Second, platelets were isolated and purified from 30 ml of blood obtained from Hartley strain guinea pigs by differential centrifugation using standard methods. The final packed undegranulated platelet cell pellet was resuspended in 3 ml of Tyrodes buffered saline (TBS). Third, composites were prepared containing three different dilutions of platelets by: (a) mixing 1 ml of platelets with 2 ml of FC-H giving a final platelet dilution of 1/12 (FC-H/PL-12); (b) diluting platelets 1/10 with TBS and then mixing 1 ml of platelets with 2 ml FC-H (FC-H/PL-120); or, (c) diluting platelets 1/1000 with TBS and then mixing 1 ml of platelets with 2 ml of FC-H (FC-H/PL-1200). Control materials were also prepared containing 1 ml of platelets mixed with 2 ml of FC (rather than FC-H).

B. PREPARATION OF COLLAGEN-HEPARIN-PLATELET RELEASATE COMPOSITES

Platelets were isolated by differential centrifugation using standard methods. The final washed platelet cell pellet was resuspended in 25 ml of 20 mM Tris buffer, pH 7.5, containing 0.14 M NaCl, 15 mM KCl, 5 mM glucose, and 2 mM CaCl. Thrombin (7 units/ml platelets) was added to induce aggregation and release. After 10 min at room temperature the aggregated platelets were removed by centrifugation at 22610×g for 20 min at 4° C. The concentration of the platelet proteins in the releasate was determined to be 642 μg/ml by Lowry analysis. Platelet releasate was stored frozen at −70° C. until use. This releasate was tested in vitro and found to stimulate human skin fibroplast proliferation.

A portion of the platelet releasate was purified by heparin-Sepharose column chromatography as follows: five ml of platelet releasate was applied to a column (0.7×9 cm) of heparin-Sepharose CL-6B (Pharmacia, Piscatawny, N.J.) which was previously equilibrated in 20 mM Tris buffer, pH 7.6, containing 0.15 M NaCl and 1 mM $CaCl_2$. After applying the sample, the column was washed with this same buffer until all the absorbance at 278 nm had reached a background level. Protein bound on the column was eluted with 20 mM Tris, pH 7.6, containing 2.0 M NaCl and 1 mM $CaCl_2$. The resultant flow-through fraction (non-bound fraction) and 2 M NaCl eluate (bound fraction) were collected, pooled, dialyzed to 0.1 M ammonium bicarbonate, pH 8, and lyophilized. Lyophilized samples were resuspended in 20 mM Tris, pH 7.6, containing 1 mM $CaCl_2$ and the insoluble residue was removed by centrifugation. Protein concentration was determined by Lowry analysis.

Releasate or chromatographed releasate is mixed with fibrillar collagen and heparin in proportions equivalent to the packed volumes of platelets used.

C. WOUND MODEL

Wounds were created in the dermis of Hartley guinea pigs using a 6 mm biopsy punch. These wounds were filled with FC, FC-H, FC-H/PL-12, FC-H/PL-120, or FC-H/PL-1200 composites and the sites were then covered with an occlusive dermal dressing. Wound sites were surgically removed after 5 or 11 days, fixed, embedded, sectioned, and stained for histological examination using hematoxylin-eosin (H&E) or Gomori trichrome stain to visualize collagen.

D. HISTOLOGICAL EVALUATION

The following criteria were used to provide numerical evaluation of histological parameters.

The relative number of cells in the wound or subcutaneous implant sites (e.g., fibroblasts, macrophages, eosinophils, lymphocytes, plasma cells, polymorphonuclear neutrophils (PMN), macrophage giant cells, or adipocytes (fat cells) was graded on a scale of 0 to 3+, where 0 corresponded to no cells visible; 1+ was a few scattered cells; 2+ was many scattered cells; 3+ was concentrated masses containing large numbers of cells.

Vascularity of the wound and implant sites was graded on a scale of 0 to 3+, where 0 was no vessels visible; 1+ was several small vessels; 2+ was many small and a few large vessels; and 3+ was many large vessels.

The amount of new host collagen was graded on a scale of 0 to 3+, where new collagen (defined as lightly staining microfibrillar in architecture) filling up to ⅓ of the wound area was graded 1+; new collagen filling ⅓ to ⅔ of the wound area was graded 2+; and new collagen filling more than ⅔ of the wound area was graded 3+.

Epithelial maturation was also graded on a scale of 0 to 3+, where thin epithelium composed of flat cells was rated 1+; thicker epithelium with less flattened basal cells and a slight development of the stratum granulosum was graded 2+; and thick epithelium with rounded basal cells, a well developed granulosum, and extensive cornification was graded 3+. An ocular micrometer was used at an objective magnification of 4× to measure the length of the epithelium and the width of wounds. These data are reported in ocular micrometer units where 0.23 mm=1 ocular unit.

Table 1 summarizes the cellular response observed in the wound sites. The data presented in Table 1 are presented graphically in FIGS. 1 through 4.

TABLE 1

Histological and Morphometric Analysis of Cellularity of Decmal Wounds: Mean Score

| Characteristic | Days | FC-H/PL | | | | FC/PL | | | |
|---|---|---|---|---|---|---|---|---|---|
| | | 1/12 | 1/120 | 1/1200 | None | 1/12 | 1/120 | 1/1200 | None |
| Fibrosis | 5 | 2.7 | 2 | 1.3 | 1 | 2 | 1 | 1 | 1 |
| Vascularity | 5 | 2.3 | 2.3 | 1.7 | 2.7 | 2.3 | 2 | 2 | 1 |
| Epidermal Length | 5 | 8.0 | 7.8 | 9.5 | 4.5 | 4.7 | 8.5 | 6.4 | 2.7 |
| (X +/− SE) | +/− | 1.0 | 0.6 | 1.0 | 1.6 | 1.9 | 0.5 | — | 1 |
| Mid-decmal Wound Width | 5 | 9.5 | 9.0 | 9.2 | 7.9 | 9.3 | 9.8 | 9.8 | 6.0 |
| (X +/− SE) | +/− | 1.2 | 0.8 | 0.5 | 0.8 | 0.8 | 0.3 | 1.8 | 0 |
| Percentage Epidermis* | 5 | 45 | 43 | 62 | 34 | 22 | 43 | 45 | 35 |
| (X +/− SE) | +/− | 7 | 4 | 8 | 20 | 4 | 4 | — | 18 |
| Fibrosis | 11 | 3 | 2.7 | 3 | 2.7 | 2.7 | 2.5 | 2 | 2 |
| Vascularity | 11 | 2.3 | 2.3 | 1.7 | 1.3 | 2 | 2 | 2 | 2 |
| Percentage Epidermis* | 11 | 100 | 100 | 100 | 100 | 100 | 100 | 100 | 100 |
| Epithelial Quality | 11 | 2.7 | 2.3 | 2 | 1.7 | 2.7 | 3 | 1.7 | 1.7 |
| (X +/− SE) | +/− | 0.3 | 0.7 | 0.6 | 0.3 | 0 | 0.3 | 0.3 | |
| Mid-decmis Wound Width | 11 | 10.5 | 7 | 6.7 | 7.8 | 9.5 | 9.8 | 11.3 | 8.8 |

TABLE 1-continued

Histological and Morphometric Analysis of
Cellularity of Decmal Wounds: Mean Score

| Characteristic | Days | FC-H/PL | | | | FC/PL | | | |
| --- | --- | --- | --- | --- | --- | --- | --- | --- | --- |
| | | 1/12 | 1/120 | 1/1200 | None | 1/12 | 1/120 | 1/1200 | None |
| (X +/− SE) | +/− | 0.5 | 0.3 | 0.2 | 0.6 | 1.3 | 1.3 | 1 | 1.3 |

*Percentage Epidermis - epidermal length/wound width at the surface X 100%.

E. Discussion of Results Shown in Table 1 and FIGS. 1-4

1. Dermal Wound Sites—Day 5 a. Fibrillar Collagen with Heparin and Platelets (FC-H/PL): Day 5

Figure 2:
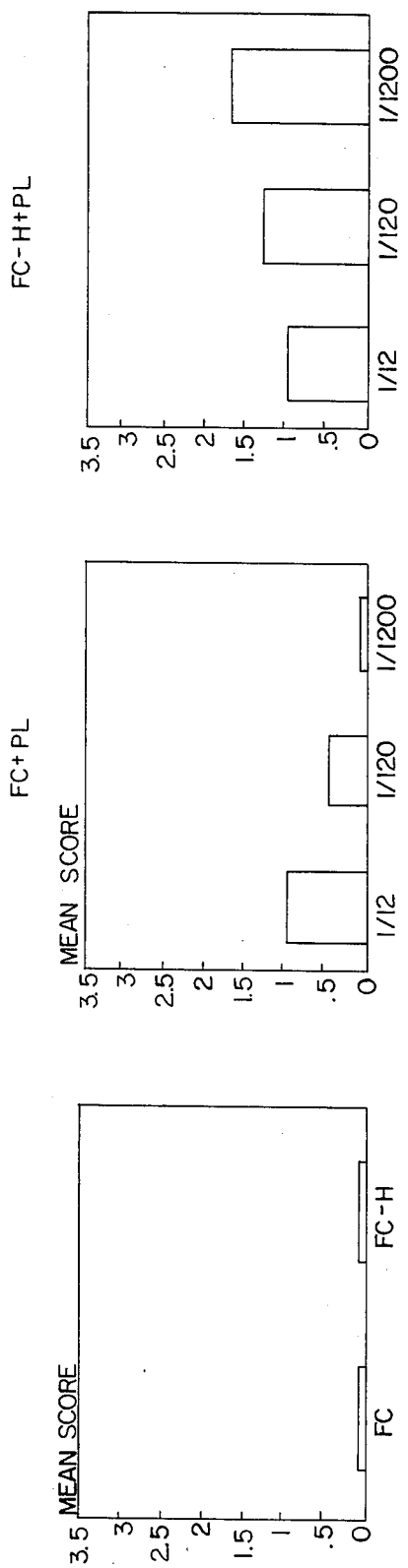
FIG. 2 is a set of bar graphs of results of the histological examination reported infra showing the vascularization evident in histological sections of wound sites treated with various test compositions.
Figure 3:
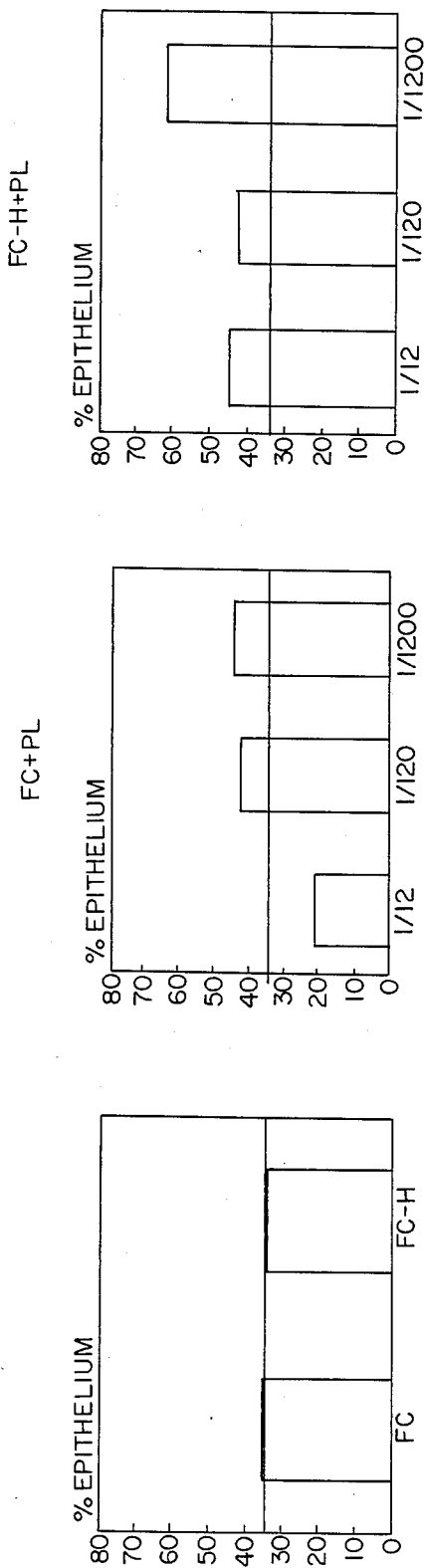
FIG. 3 is a set of bar graphs of results of the histological examination reported infra showing the re-epithelialization evident in histological sections of wound sites treated with various test compositions.
Figure 4:
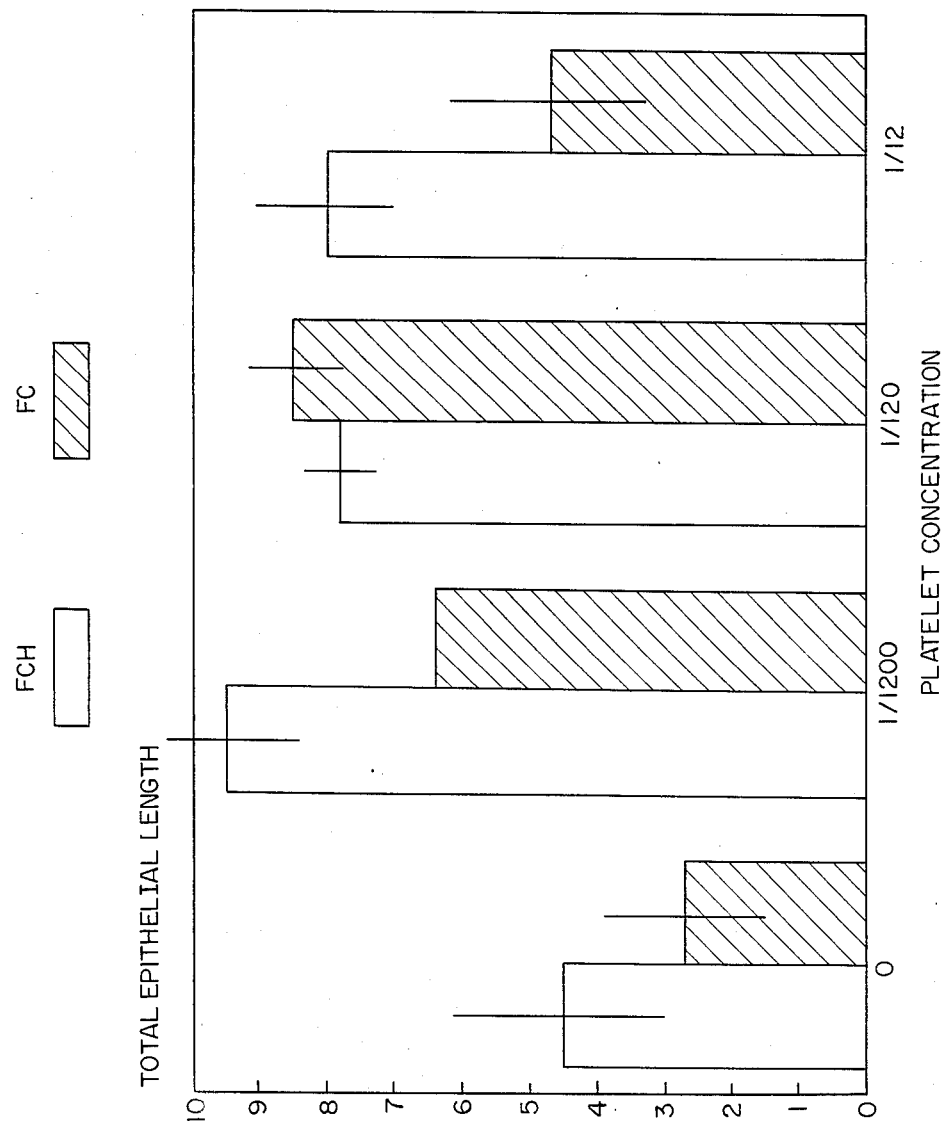
FIG. 4 is a set of bar graphs of results of the histological examination reported infra showing total epithelial length (in ocular micrometer units) evident in histological sections of wound sites treated with various test compositions.

Granulation tissue deposition, fibrosis, new host collagen, and neo-vascularization of wounds was increased at higher doses of platelets (Table 1, FIGS. 1–2). Morphometric measurements presented in Table 1 and FIGS. 3 and 4 show the percentage of the wound covered by new epithelium and the total length of newly formed epithelium on day 5. Wounds treated with FC-H/PL had greater amounts of new epithelium than wounds without platelets. This difference was statistically significant ($P=0.02$). The measured difference of the platelet-treated wound sites was also greater than that of the non-platelet treated wounds at the wound surface and at the level of the mid-dermis. It is important that while relatively small percentage differences in re-epithelialization were observed in the FC-H/PL treated wound sites (FIG. 3) the actual length of new epithelium was 1.7–2.1 times greater than control FC-H treated sites and 2.9–3.5 times greater than FC treated wound sites. The reason for this apparent disparity in measurements almost certainly lies within the finding of greater mid-dermis measurements in platelet/FC-H treated wounds (Table 1), a finding which suggests less wound contracture in these treated sites and hence a much longer expanse of wound surface which must be covered by new epithelium. Treatment of wound sites with FC-H resulted in granulation tissue deposition which appeared more extensive than that in wound sites treated with FC alone, however, this was not confirmed in morphometric analyses (Table 1, FIG. 1). At higher doses of platelets (i.e., 1/12), composite material visible in the tissue sections was broken up into smaller, less dense islands of material through infiltration of fibroblasts.

Inflammation of sites with PMN and lymphocytes was minimal with all composites and the extent of inflammation did not appear related to the dosage of platelets in the wound sites. Giant cells were occasionally observed, however, these were not associated with the implant material, nor were giant cells more prevalent in implant materials formulated with platelets. No eosinophils, plasma cells, or fat cells were observed.

b. Fibrillar Collagen with Platelets (FC/PL): Day 5

The results also presented in Table 1 summarize the histological findings at wound sites filled with FC with and without platelets. Wounds with higher concentrations of platelets had greater fibroplasia (FIG. 1) and more small blood vessels (FIG. 2) than controls receiving FC or FC-H alone. Epithelialization was incomplete but the length of new epithelial surface was greater in the platelet containing wounds than in control FC wounds (Table 1, FIGS. 3–4); FC/PL containing wounds showed greater re-epithelialization than FC-H wounds lacking platelets, but less than FC-H/PL. The FC composite was visible as large, dense and homogeneous masses of collagen with a fine fibrillar substructure. A few clefts or irregular spaces were visible within the composite. The inclusion of platelets in the composite resulted in a separation of the composite into smaller islands of material separated by infiltrating fibroblasts and new collagen. Small numbers of lymphocytes, PMN, or giant cells were seen within the composite (Table 2). There were no eosinophils, plasma cells, or fat cells visible.

2. Dermal Wound Sites—Day 11 a. Fibrillar Collagen with Heparin and Platelets: Day 11

Histological differences among wounds with different doses of platelets were less pronounced at day 11 than at day 5 (above). All wounds were completely covered by new epithelium and the quality of the epithelium appeared to be related to the number of platelets in the composite, with higher epithelial quality being associated with larger numbers of platelets (Table 1). In these cases the epidermis was thicker, with more rounded basal cells and there was increased differentiation with a more pronounced kerato-hyalin layer and increased cornification. In all wounds less composite was visible than at day 5, and the composite was well infiltrated by fibroblasts. Equivalent amounts of granulation tissue and new collagen were seen in the various groups (Table 1). Wounds treated with higher concentrations of platelets appeared more vascular, however, this was not confirmed in numerical analyses (Table 1). A minimal inflammatory profile was observed: namely, only a few lymphocytes, macrophages, giant cells, and pyknotic neutrophils were observed in these tissue sections.

b. Fibrillar Collagen with Platelets: Day 11

All wounds appeared to be completely re-epithelialized. The quality of the epithelium was notably better in wound sites treated with FC-platelet composites (Table 1). In these cases the epidermis was thicker, with more rounded basal cells, and there was notably greater differentiation of the epidermis with a more pronounced kerato-hyalin layer and increased cornification (Table 1). Fibroplasia and neo-vascularization did not appear to be more pronounced in wound sites treated with FC-platelets than in control wound sites. FC composites were more dispersed at the higher platelet dosages, apparently due to division of the composite by infiltrating fibroblasts. New host collagen synthesis was visible in sites. Small numbers of lymphocytes, giant cells, and pyknotic neutrophils were observed. No plasma cells were noted.

In addition to the histological evaluations, serological evaluations of the animals were made using blood taken at sacrifice and an ELISA for antibodies to the collagen or collagen-platelet composites. No animal developed antibodies to the collagen or the composites. Samples of the composites were also placed in subcutaneous tissue sites in the same animals immediately adjacent the wound sites. The implants were removed after 5 or 11 days. No significant fibroplasia, new collagen formation, inflammation or fibrous encapsulation of the implants were observed thus ruling out the possibility of uncontrolled growth.

In over two years of testing various biomaterials in the guinea pig model described above, the platelet-containing composites were the only materials that have exhibited a significant enhancement in rate of wound healing. The data also show that the composites enhance the extent of wound healing (platelet/FC-H composites inhibit wound contracture). If contracture is related to the formation of keloids or hypertrophic scars, then the composites may provide a mechanism for healing without scarring.

Modifications of the above-described modes for carrying out the invention that are obvious to those of skill in the fields of medicine, surgery, biochemistry, and related fields are intended to be within the scope of the following claims.

We claim:

1. A soft tissue wound healing composition comprising an aqueous mixture of:
   (a) fibrillar collagen at a concentration in the range of about 1 to about 70 mg/ml;
   (b) about 0.1% to about 10% by weight based on collagen of a glycosaminoglycan selected from the group consisting of heparin, a heparin-like glycosaminoglycan, and mixtures thereof; and
   (c) about 0.01% to about 10% by volume based on collagen of undegranulated platelets or an equivalent amount of platelet releasate.

2. A composition for promoting fibroplasia at a soft tissue wound site comprising an aqueous mixture of:
   (a) fibrillar collagen at a concentration in the range of about 1 to about 70 mg/ml;
   (b) about 0.1% to about 10% by weight based on collagen of a glycosaminoglycan selected from the group consisting of heparin, a heparin-like glycosaminoglycan, and mixtures thereof; and
   (c) about 0.01% to about 10% by volume based on collagen of undegranulated platelets or an equivalent amount of platelet releasate.

3. A composition for promoting reepithelialization at a soft tissue wound site comprising an aqueous mixture of:
   (a) fibrillar collagen at a concentration in the range of about 1 to about 70 mg/ml;
   (b) about 0.1% to about 10% by weight based on collagen of a glycosaminoglycan selected from the group consisting of heparin, a heparin-like glycosaminoglycan, and mixtures thereof; and
   (c) about 0.01% to about 10% by volume based on collagen of undegranulated platelets or an equivalent amount of platelet releasate.

4. A composition for promoting vascularization at a soft tissue wound site comprising an aqueous mixture of:
   (a) fibrillar collagen at a concentration in the range of about 1 to about 70 mg/ml;
   (b) about 0.1% to about 10% by weight based on collagen of a glycosaminoglycan selected from the group consisting of heparin, a heparin-like glycosaminoglycan, and mixtures thereof; and
   (c) about 0.01% to about 10% by volume based on collagen of undegranulated platelets or an equivalent amount of platelet releasate.

5. A cutaneous wound healing composition comprising an aqueous mixture of:
   (a) fibrillar collagen at a concentration in the range of about 1 to about 70 mg/ml;
   (b) about 0.1% to about 10% by weight based on collagen of heparin; and
   (c) about 0.01% to about 10% by volume based on collagen of undegranulated platelets or an equivalent amount of platelet releasate.

6. The composition of claim 5 wherein the collagen is Type I collagen, Type III collagen, or mixtures thereof.

7. The composition of claim 6 wherein the fibrillar collagen is reconstituted fibrillar collagen.

8. The composition of claim 5 wherein the concentration of fibrillar collagen is in the range of 15 to 35 mg/ml.

9. The composition of claim 5 wherein the amount of heparin in the composition is in the range of 0.3% to 3% by weight based on collagen and the amount of undegranulated platelets is 2% to 10% by volume based on collagen and the amount of platelet releasate is equivalent to said amount of undegranulated platelets.

10. The composition of claim 5 wherein the collagen is reconstituted xenogeneic collagen, the concentration of collagen is in the range of 15 to 35 mg/ml, the heparin constitutes about 1% by weight based on collagen, and the amount of undegranulated platelets is about 2% to 10% by volume based on collagen and the amount of platelet releasate is equivalent to said amount of undegranulated platelets.

11. A cutaneous wound dressing comprising a composite of
   (a) a solid support on which is carried
   (b) the composition of claim 5.

12. A cutaneous wound dressing comprising a composite of
   (a) a solid support on which is carried
   (b) the composition of claim 6.

13. A cutaneous wound dressing comprising a composite of
   (a) a solid support on which is carried
   (b) the composition of claim 7.

14. A cutaneous wound dressing comprising a composite of
   (a) a solid support on which is carried
   (b) the composition of claim 8.

15. A cutaneous wound dressing comprising a composite of
   (a) a solid support on which is carried
   (b) the composition of claim 9.

16. A cutaneous wound dressing comprising a composite of
   (a) a solid support on which is carried
   (b) the composition of claim 10.

17. A method of promoting healing of a soft tissue wound comprising applying the composition of claim 1 to the wound site in conjunction with means for keeping the composition at the site and hydrated.

18. The method of claim 17 wherein the soft tissue wound is a cutaneous wound, a dermal wound, a mucosal wound, or an epithelial wound.

19. A method of promoting healing of a cutaneous wound comprising applying the composition of claim 5 to the wound site in conjunction with a dressing that keeps the composition at the site and hydrated.

20. A method of promoting healing of a cutaneous wound comprising applying the composition of claim 6 to the wound site in conjunction with a dressing that keeps the composition at the site and hydrated.

21. A method of promoting healing of a cutaneous wound comprising applying the composition of claim 7 to the wound site in conjunction with a dressing that keeps the composition at the site and hydrated.

22. A method of promoting healing of a cutaneous wound comprising applying the composition of claim 8 to the wound site in conjunction with a dressing that keeps the composition at the site and hydrated.

23. A method of promoting healing of a cutaneous wound comprising applying the composition of claim 9 to the wound site in conjunction with a dressing that keeps the composition at the site and hydrated.

24. A method of promoting healing of a cutaneous wound comprising applying the composition of claim 10 to the wound site in conjunction with a dressing that keeps the composition at the site and hydrated.

* * * * *